United States Patent
Amano et al.

(10) Patent No.: US 6,903,233 B2
(45) Date of Patent: Jun. 7, 2005

(54) PROCESS FOR PRODUCING OPTICALLY ACTIVE 3-HALOGENOCARBOXYLIC ACID ESTER AND 3-AZIDOCARBOXYLIC ACID ESTER

(75) Inventors: Akira Amano, Hiratsuka (JP); Daisuke Igarashi, Hiratsuka (JP); Takashi Miura, Tokyo (JP)

(73) Assignee: Takasago International Corporation, Tokyo (JP)

(*) Notice: Subject to any disclaimer, the term of this patent is extended or adjusted under 35 U.S.C. 154(b) by 106 days.

(21) Appl. No.: 10/383,866

(22) Filed: Mar. 10, 2003

(65) Prior Publication Data

US 2003/0225301 A1 Dec. 4, 2003

(30) Foreign Application Priority Data

Mar. 11, 2002 (JP) .................................... 2002-065728
Apr. 5, 2002 (JP) .................................... 2002-103547

(51) Int. Cl.$^7$ .................... C07C 205/00; C07C 229/00; C07C 247/04; C07C 69/62; C09K 19/52
(52) U.S. Cl. .................. 562/553; 252/299.01; 552/12; 560/155; 560/179; 560/226
(58) Field of Search .................. 252/299.01; 552/12; 560/155, 179, 226; 562/553

(56) References Cited

U.S. PATENT DOCUMENTS

| | | | |
|---|---|---|---|
| 4,334,083 A | 6/1982 | Buathier et al. | ............ 560/226 |
| 4,855,455 A | 8/1989 | Kupper | ........................ 549/88 |
| 4,874,544 A | 10/1989 | Yong et al. | ............ 252/299.61 |

FOREIGN PATENT DOCUMENTS

| | | |
|---|---|---|
| JP | 63-222148 A | 9/1988 |
| JP | 2912375 B2 | 4/1999 |
| JP | 11-246472 A | 9/1999 |

OTHER PUBLICATIONS

Seebach, Dieter, et al.; α–Alkylation of β–Aminobutanoates with lk–1.2–Induction; Tetrahedron Letters; vol. 28, No. 27, pp. 3103–3106; 1987.

Kitamura, M., et al.; Homogeneous Asymmetric Hydrogenation of Functionalized Ketones; J. Am. Chem. Soc.; vol. 110, No. 2, pp. 629–631; 1988.

Tanaka, Yoshio, et al.; Asymmetric Halogenation and Hydrohalogenation of trans–2–Butenoic Acid in a Crystalline α–Cyclodextrin Complex; J. Org. Chem.; vol. 55, No. 2, pp. 564–567; 1990.

Pye, Philip J., et al.; PHANEPHOS–Ruthenium(II) Complexes: Highly Active Asymmetric Catalysts for the Hydrogenation of β–Ketoesters; Tetrahedron Letters; pp. 4441–4444; 1998.

R&D Program for "Next–generation Chemical Process Technology, R&D Project for Process Utilizing Mutli–phase Catalytic Systems, NEDO Annual Project Report 2000 (Heisei–13)"; The Japan Chemical Innovation Institute; pp. 33–45; Jun. 2001.

Kenyon, J., et al.; "Walden Inversion Reactions of the p–Toluenesulphinic and the p–Toluenesulphonic Esters of Ethyl d–β–Hydroxy–β–phenylpropionate"; J. Chem. Soc.; pp. 1663–1668; 1935.

Kasina, S., et al.; "Tissue Distribution Properties of Technetium–99m–Diamide–Dimercaptide Complexes and Potential Use as Renal Radiopharmaceuticals"; Journal of Medicinal Chemistry, American Chemical Society; vol. 29, No. 10, pp. 1933–1940; Oct. 1, 1986.

Collins, J. L., et al.; "N–(2–Benzoylphenyl)–L–tyrosine PPARγ Agonists. 2. Structure–Activity Relationship and Optimization of the Phenyl Alkyl Ether Moiety"; Journal of Medicinal and Pharmaceutical Chemistry, American Chemical Society; vol. 41, No. 25, pp. 5037–5054; 1998.

Primary Examiner—Shean C. Wu
(74) Attorney, Agent, or Firm—Kubovcik & Kubovcik

(57) ABSTRACT

A process for producing an optically active 3-azide-carboxylic acid ester by reacting an optically active 3-hydroxycarboxylic acid ester and a thionyl halide in the presence of a basic substance in an organic solvent to produce an optically active 3-halogenocarboxylic acid ester which is then reacted with an azide salt represented by the formula: $MN_3$ (wherein M is an alkaline metal) in water or a mixture of water and a water soluble organic solvent.

17 Claims, No Drawings

PROCESS FOR PRODUCING OPTICALLY ACTIVE 3-HALOGENOCARBOXYLIC ACID ESTER AND 3-AZIDOCARBOXYLIC ACID ESTER

FIELD OF THE INVENTION

The present invention relates to a process for producing an optically active 3-halogenocarboxylic acid ester and 3-aminocarboxylic acid ester which are useful as an intermediate for medicines, sweeteners, liquid crystal materials, and the like.

BACKGROUND OF THE INVENTION

In recent years, an optically active compound has been widely used for medicines, pesticides, sweeteners, liquid crystal materials, and the like. Various methods to manufacture the optically active compound have been researched and developed. For example, development of a special catalyst, and study of separation or disposal of unnecessary isomers has been conducted.

An optically active 3-chlorocarboxylic acid derivative which is halogenized at a β-position of a carboxylic acid is known as one of optically active compounds.

Known processes for producing optically active 3-chlorocarboxylic acid derivatives include:
(1) a process for producing an optically active 3-chlorocarboxylic acid in which hydrogen chloride is added to an α,β-unsaturated carboxylic acid by an addition reaction in the presence of cyclodextrin [J. Org. Chem., 55, 564 (1990)]; and
(2) a process for producing an optically active 3-chlorocarboxylic acid ester in which an optically active 3-hydroxycarboxylic acid ester and thionyl chloride are reacted in the presence of a catalytic amount of zinc chloride (Japanese patent Laid-open publication No. 63-222148; especially Example 4).

However, there are problems that the method (1) described above requires a long reaction, gives a low yield, and provides a low optical purity of the optically active 3-chlorocarboxylic acid. There are also various problems in the method (2) described above, that is, the method requires use of an excess amount of thionyl chloride and a long reaction time, gives a low yield, and uses a heavy metal salt as a catalyst. Besides such problems, there is no guarantee to be able to obtain a highly optically active 3-chlorocarboxylic acid ester.

An invention disclosed in Japanese patent Laid-open publication No. 11-246472 relates to a process for producing an optically active α-substituted carboxylic acid in which an optically active α-substituted carboxylic acid ester is used as a starting material, the optically active α-substituted carboxylic acid ester is contacted with an organic acid in the presence of an inorganic acid catalyst. A process for producing methyl D-2-chloropropionate, which is one of the optically active α-substituted carboxylic acid esters (the starting material of the process described above), in which L-methyl lactate and thionyl chloride are reacted without a solvent in the presence of a catalytic amount of pyridine is described in Example 1 of the publication.

However, according to the process described in Example 1 of the publication, the yield of methyl D-2-chloropropionate is not high.

The process described in Example 1 of the publication has been applied to production of an optically active 3-halogenocarboxylic acid ester (by the inventors of the present invention). The yield of the objective compound, i.e., 3-halogenocarboxylic acid ester, is low. An optically active 3-halogenocarboxylic acid ester having a high optical purity cannot be obtained at a high yield, that is, productivity by the process is not good.

An optically active 3-azido-carboxylic acid derivative which is obtained by azidizing a carboxylic acid at β-position and an optically active 3-aminocarboxylic acid ester which is obtained by hydrogenating the azide compound are known as optically active compounds in the same category (group) described above.

As a process for producing an optically active 3-azido-carboxylic acid ester, a process in which an optically active methyl 3-hydroxybutanoate is reacted with p-toluenesulfonyl chloride in pyridine to obtain an optically active methyl 3-(p-toluenesulfonyloxy)butanoate, and then the optically active methyl 3-(p-toluenesulfonyloxy) butanoate is reacted with sodium azide to obtain an optically active methyl 3-azide-butanoate, is known ("Tetraherdon Lett.", 28, 3103 (1987), R&D Program for "Next-generation Chemical Process Technology, R&D Project for Process Utilizing Multi-phase Catalytic Systems, NEDO Annual Project Report 2000 (Heisei-13)", pp. 33–45, The Japan Chemical Innovation Institute, Published June, 2001). In the above-mentioned "Tetraherdon Lett.", a process for producing an optically active methyl 3-azide-butanoate by hydrogenating an optically active methyl 3-aminobutanoate is described.

However, there are problems in the commonly used processes explained above such as the reaction of the optically active methyl 3-hydroxybutanoate with p-toluenesulfonyl chloride being required to be performed in the presence of an excess amount of pyridine to produce the optically active methyl 3-(p-toluenesulfonyloxy)butanoate which is used as a starting material, and a side product of azidation, sodium p-toluenesulfonate, is necessary to be treated as a waste.

In the above-mentioned "Next Generation Chemical Process Techniques Development, Development of Multi-phase Catalyst Reaction Process Technique, Report of Completion in 2000 (Heisei-13)", there is a description that the reaction of the optically active methyl 3-(p-toluenesulfonyloxy) butanoate and sodium azide is performed in (a) N,N-dimethylformamide, (b) a water-toluene system, or (c) a water-polyethylene glycol (interphase mobile catalyst phase)-toluene system. However, if the reaction is performed in (a), it is difficult to separate synthesized 3-azido-carboxylic acid ester from N,N-dimethylformamide because the boiling point of N,N-dimethylformamide used as the solvent is high. Moreover, sodium azide is not dissolved in N,N-dimethylformamide so that sodium azide has to react with the optically active methyl 3-(p-toluenesulfonyloxy) butanoate as a solid. Therefore, it is difficult to perform the reaction smoothly. If the reaction is performed in (b), a conversion rate from the optically active methyl 3-(p-toluenesulfonyloxy)butanoate to an azide compound is small, and the obtained optically active methyl 3-azide-butanoate does not have sufficient optical purity. If the reaction in (c) is performed, a conversion rate is better than that of the reaction performed in (b), but optical purity of the obtained optically active methyl 3-azide-butanoate is still not satisfactory high.

Japanese Patent No. 2912375 discloses a process for producing an optically active α-azide-carboxylic acid ester (concretely (R)-ethyl-2-azide-propionate) in which an optically active α-hydroxycarboxylic acid ester (an optically active 2-α-hydroxycarboxylic acid ester) which has a hydroxy group at the α-position and not the β-position is used as a starting material, the hydroxy group is converted to a p-toluenesulfonyloxy group, and is reacted with sodium azide to obtain the objective compound. However, this process also requires treatment of a side product of sodium p-toluenesulfonate as waste, and it is not guaranteed that an optically active α-azide-carboxylic acid ester having a high optical purity can be obtained.

OBJECTS OF THE INVENTION

An object of the present invention is to provide a process for producing an optically active 3-halogenocarboxylic acid ester having a high optical purity efficiently in a short reaction time and with a high yield.

Another object of the present invention is to provide a process for producing efficiently an optically active 3-azide-carboxylic acid ester and an optically active 3-aminocarboxylic acid ester having a high optical purity at a high yield with less waste that is required to be treated.

SUMMARY OF THE INVENTION

The inventors have conducted research to accomplish the above objects. It has been found that when an optically active 3-hydroxycarboxylic acid ester and thionyl halide are reacted in the presence of a basic substance, an optically active 3-halogenocarboxylic acid ester having a high optical purity can be obtained in a short reaction time and with a high yield and the present invention has been completed.

The inventors found that when an optically active 3-halogenocarboxylic acid ester is used as a starting material, instead of an optically active 3-(p-toluenesulfonyloxy)carboxylic acid ester, and is azidized with an azide salt (for example, sodium azide, and the like) in water to produce an optically active 3-azide-carboxylic acid ester, it is possible to eliminate production of sodium p-toluenesulfonate as a side product. Additionally, the objective optically active 3-azide-carboxylic acid ester having a high optical purity can be obtained at a high yield.

Further, the inventors found that when the above mentioned reaction is performed in an aqueous solution comprising a mixture solution of water and water soluble organic solvent, production of sodium p-toluenesulfonate as a side product can be eliminated, and the objective optically active 3-azide-carboxylic acid ester having a high optical purity can be obtained at a high yield.

The inventors also found that when the reaction in the aqueous solution comprising the mixture of water and water soluble organic solvent is followed by hydrogenation of the obtained optically active 3-azide-carboxylic acid ester, an optically active 3-aminocarboxylic acid ester having a high optical purity can be obtained at a high yield.

The inventors also found that when the reaction of the optically active 3-halogenocarboxylic acid ester and the azide salt is performed in the aqueous solution comprising the mixture of water and water soluble organic solvent, unreacted azide salt can be easily and efficiently separated and recovered as an aqueous phase in which the unreacted azide is dissolved. The separated and recovered aqueous phase containing the unreacted azide salt can be reused for the azidation of the optically active 3-halogenocarboxylic acid ester to produce an optically active 3-azide-carboxylic acid ester. Even such reuse of the aqueous phase containing unreacted azide salt provides an optically active 3-azide-carboxylic acid ester having a high optical purity with a high yield. The present invention has been completed on the basis of the results explained above.

The following are processes of the present inventions.

(1) A process for producing an optically active 3-azide-carboxylic acid ester characterized in that an optically active 3-hydroxycarboxylic acid ester represented by the following formula (I);

(I)

(wherein $R^1$ is alkyl, substituted alkyl, aralkyl or substituted aralkyl; $R^2$ is lower alkyl; and * is an asymmetric carbon) and a thionyl halide are reacted in the presence of a basic substance in an organic solvent to produce an optically active 3-halogenocarboxylic acid ester represented by the following formula (II);

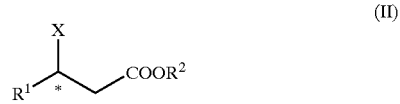

(II)

(wherein X is halogen, $R^1$, $R^2$ and * are defined above); and the optically active 3-halogenocarboxylic acid ester represented by the formula (II) is reacted with an azide salt represented by the formula: $MN_3$ (wherein M is an alkaline metal) in an aqueous solvent to produce an optically active 3-azide-carboxylic acid ester represented by the following formula (III);

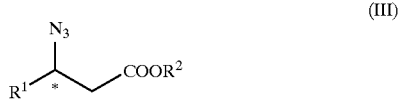

(III)

(wherein $R^1$, $R^2$ and * are defined above).

(2) A process for producing an optically active 3-aminocarboxylic acid ester characterized in that an optically active 3-hydroxycarboxylic acid ester represented by the following formula (I);

(I)

(wherein $R^1$ is alkyl, substituted alkyl, aralkyl or substituted aralkyl; $R^2$ is lower alkyl; and * is an asymmetric carbon) and a thionyl halide are reacted in the presence of a basic substance in an organic solvent to produce an optically active 3-halogenocarboxylic acid ester represented by the following formula (II);

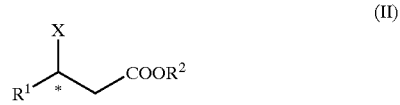

(II)

(wherein X is halogen, $R^1$, $R^2$ and * are defined above); and the optically active 3-halogenocarboxylic acid ester represented by the formula (II) is reacted with an azide salt represented by the formula: $MN_3$ (wherein M is an alkaline metal) in an aqueous solvent to produce an optically active 3-azide-carboxylic acid ester represented by the following formula (III);

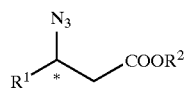
(III)

(wherein $R^1$, $R^2$ and * are defined above); and then the 3-azide-carboxylic acid ester is hydrogenated in the presence of a hydrogenating catalyst to produce an optically active 3-aminocarboxylic acid ester represented by the formula (IV);

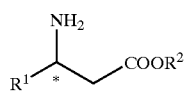
(IV)

(wherein $R^1$, $R^2$ and * are defined above).

(3) A process for producing an optically active 3-halogenocarboxylic acid ester characterized in that an optically active 3-hydroxycarboxylic acid ester represented by the following formula (I);

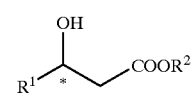
(I)

(wherein $R^1$ is alkyl, substituted alkyl, aralkyl or substituted aralkyl; $R^2$ is lower alkyl; and * is an asymmetric carbon) and a thionyl halide are reacted in the presence of a basic substance in an organic solvent to produce an optically active 3-halogenocarboxylic acid ester represented by the following formula (II);

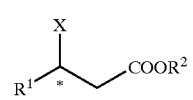
(II)

(wherein X is halogen, $R^1$, $R^2$ and * are defined above).

(4) A process for producing an optically active 3-chlorocarboxylic acid ester described in (3) above wherein thionyl chloride is used as the thionyl halide to produce an optically active 3-chlorocarboxylic acid ester represented by the formula (IIa);

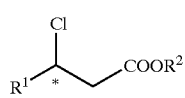
(IIa)

(wherein $R^1$ is alkyl, substituted alkyl, aralkyl or substituted aralkyl; $R^2$ is lower alkyl; and * is an asymmetric carbon).

(5) The process described above (3) wherein the basic substance is an amine.

(6) A process for producing an optically active 3-azide-carboxylic acid ester characterized in that an optically active 3-halogenocarboxylic acid ester represented by the following formula (II);

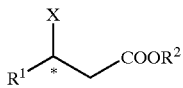
(II)

(wherein X is halogen; $R^1$ is alkyl, substituted alkyl, aralkyl or substituted aralkyl; $R^2$ is lower alkyl; and * is an asymmetric carbon) is reacted in an aqueous solvent with an azide salt represented by the formula: $MN_3$ (wherein M is an alkaline metal) to produce an optically active 3-azide-carboxylic acid ester represented by the following formula (III);

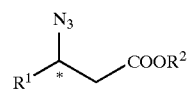
(III)

(wherein $R^1$, $R^2$ and * are defined above).

(7) The process described in (6) above wherein the aqueous solvent is water.

(8) The process described in (6) above wherein the aqueous solvent is a mixture of water and water soluble organic solvent.

(9) The process described in (8) above wherein the water soluble organic solvent is a polyvalent alcohol (polyol).

(10) The process described in (6) above wherein the azide salt used for producing the optically active 3-azide-carboxylic acid ester represented by the formula (III) is recovered from a reaction mixture containing the produced optically active 3-azide-carboxylic acid ester.

(11) The process described in (6) above wherein the azide salt used for production of the optically active 3-azide-carboxylic acid ester represented by the formula (III) is recovered from a reaction mixture containing the produced optically active 3-azide-carboxylic acid ester, and the recovered azide salt is used again for reaction with an optically active 3-halogenocarboxylic acid ester represented by the formula (II).

(12) The process described above (6) wherein the azide salt is recovered as an aqueous phase with the aqueous solvent.

(13) A process for producing an optically active 3-aminocarboxylic acid ester characterized in that an optically active 3-halogenocarboxylic acid ester represented by the following formula (II);

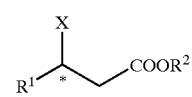
(II)

(wherein X is halogen; $R^1$ is alkyl, substituted alkyl, aralkyl or substituted aralkyl; $R^2$ is lower alkyl; and * is an asymmetric carbon) is reacted in an aqueous solvent with an azide salt represented by the formula: $MN_3$ (wherein M is an alkaline metal) to produce an optically active 3-azide-carboxylic acid ester represented by the following formula (III);

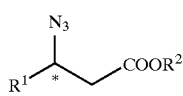

(III)

(wherein R¹, R² and * are defined above); and then the optically active 3-azide-carboxylic acid ester is hydrogenated in the presence of a hydrogenating catalyst to produce an optically active 3-aminocarboxylic acid ester represented by the formula (IV);

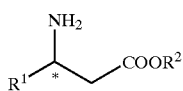

(IV)

(wherein R¹, R² and * are defined above).

(14) The process described above (13) wherein the aqueous solvent is water.

(15) The process described above (13) wherein the aqueous solvent is a mixture of water and water soluble organic solvent.

(16) The process described above (15) wherein the water soluble organic solvent is a polyvalent alcohol (polyol).

(17) The process described above (13) wherein the azide salt used for producing the optically active 3-azide-carboxylic acid ester represented by the formula (III) is recovered from a reaction mixture containing the produced optically active 3-azide-carboxylic acid ester.

(18) The process described in (13) above wherein the azide salt used for production of the optically active 3-azide-carboxylic acid ester represented by the formula (III) is recovered from the reaction mixture containing the produced optically active 3-azide-carboxylic acid ester, and the recovered azide salt is used again for reaction with an optically active 3-halogenocarboxylic acid ester represented by the formula (II).

(19) The process described in (13) above wherein the azide salt is recovered as an aqueous phase with the aqueous solvent.

(20) The process described in (6) or (13) above wherein the optically active 3-halogenocarboxylic acid ester represented by the formula (II) is an optically active 3-chlorocarboxylic acid ester represented by the formula (IIa);

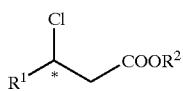

(IIa)

(wherein R¹ is alkyl, substituted alkyl, aralkyl or substituted aralkyl; R² is lower alkyl; and * is an asymmetric carbon).

DETAILED EXPLANATION OF THE INVENTION

An optically active 3-hydroxycarboxylic acid ester (hereinafter referred to as optically active 3-hydroxycarboxylic acid ester (I)) used as a starting material of the present invention is represented by the following formula (I);

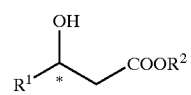

(I)

wherein R¹ is alkyl, substituted alkyl, aralkyl or substituted aralkyl; R² is lower alkyl; and * is an asymmetric carbon.

An optically active 3-halogenocarboxylic acid ester (hereinafter referred to as optically active 3-halogenocarboxylic ester (II)) used in the present invention is represented by the following formula (II);

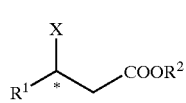

(II)

wherein X is halogen; R¹ is alkyl, substituted alkyl, aralkyl or substituted aralkyl; R² is lower alkyl; and * is an asymmetric carbon.

An optically active 3-azide-carboxylic acid ester (hereinafter referred to as optically active 3-azide-carboxylic acid ester (III)) used in the present invention is represented by the following formula (III);

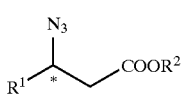

(III)

wherein R¹ is alkyl, substituted alkyl, aralkyl or substituted aralkyl; R¹ is lower alkyl and * is an asymmetric carbon.

An optically active 3-aminocarboxylic acid ester (hereinafter referred to as optically active 3-aminocarboxylic acid ester (IV)) is represented by the formula (IV);

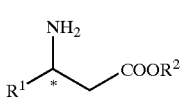

(IV)

wherein R¹ is alkyl, substituted alkyl, aralkyl or substituted aralkyl; R² is lower alkyl and * is an asymmetric carbon.

When R¹ is alkyl, the alkyl may be linear, branched or cyclic. For example, a linear, branched or cyclic alkyl having 1–10 carbon atoms can be illustrated. Methyl, ethyl, n-propyl, 2-propyl, n-butyl, 2-butyl, t-butyl, 2-methylpropyl, n-pentyl, 2-pentyl, t-pentyl, 3-methylbutyl, n-hexyl, 2-hexyl, 3-hexyl, t-hexyl, 4-methylpentyl, heptyl, octyl, 2-ethylhexyl, nonyl, decyl, cyclopropyl, cyclohexyl, and the like can be illustrated as concrete examples.

When R¹ is substituted alkyl, the alkyl has at least one hydrogen of the alkyl described above substituted by a substituting group, for example, alkoxy, or the like. The alkoxy as the substituting group can be linear or branched. For example, the alkoxy can be a linear or branched alkoxy having 1–10 carbon atoms. When R¹ is substituted alkyl, methoxy, ethoxy, propoxy, butoxy, pentyloxy, hexyloxy, heptyloxy, octyloxy, nonyloxy, decyloxy, 2-propoxy, t-butoxy, 2-ethylhexyloxy, and the like that are a linear or branched alkyl having 1–10 carbon atoms substituted by alkoxy can be illustrated.

For example, methoxymethyl, ethoxyethyl, and the like can be illustrated as alkoxyalkyl.

When $R^1$ is aralkyl, the aralkyl may have 7–18 carbon atoms. The aralkyl has at least one hydrogen of a lower alkyl having 1–4 carbon atoms, such as methyl, ethyl, n-propyl, 2-propyl, n-butyl, 2-butyl, t-butyl, 2-methylpropyl, substituted with aryl. Aryl having 6–14 carbon atoms such as phenyl, naphthyl can be illustrated. For example, benzyl, phenethyl, 3-phenylpropyl, 4-phenylbutyl, and the like can be illustrated as the aralkyl for $R^1$.

When $R^1$ is substituted aralkyl, the aralkyl has at least one hydrogen of the aryl of the aralkyl described above substituted by a substituting group. As a substituting group, a linear or branched alkyl having 1–4 carbon atoms such as methyl, ethyl, n-propyl, 2-propyl, n-butyl, 2-butyl, t-butyl, a linear or branched alkoxy having 1–4 carbon atoms such as methoxy, ethoxy, propoxy, butoxy, 2-propoxy, and halogen such as fluorine, chloride, bromine, iodine, can be illustrated. Methylbenzyl, methylphenethyl. methoxybenzyl, methoxyphenethyl, chlorobenzyl, chlorophenethyl, and the like can be illustrated as concrete examples of the substituted aralkyl.

A lower alkyl represented by $R^2$ may be linear or branched. An alkyl having 1–4 carbon atoms, for example, methyl, ethyl, n-propyl, 2-propyl, n-butyl, 2-butyl, t-butyl, 2-methylpropyl, and the like can be illustrated.

The halogen represented by X in optically active 3-halogenocarboxylic ester (II) may be fluorine, chlorine, bromine, iodine and the like. 3-chlorocarboxylic acid ester in which X is chlorine is preferable because it has an excellent reactivity with an azide salt such as sodium azide and an objective optically active 3-azide-carboxylic acid ester (III) can be produced in a high yield, and it is inexpensive.

The following compounds can be illustrated as an optically active 3-hydroxycarboxylic acid ester (I) used as a starting material:

An ester (for example, methyl ester, ethyl ester, n-propyl ester, 2-propyl ester, n-butyl ester, 2-butyl ester, t-butyl ester, 2-methylpropyl ester, and the like) of the following carboxylic acid in which $R^1$ is substituted aralkyl:

3-hydroxybutanoic acid,
3-hydroxypentanoic acid,
3-hydroxy-4-methylpentanoic acid,
3-hydroxy-4,4-dimethylpentanoic acid,
3-hydroxyhexanoic acid,
3-hydroxy-4-methylhexanoic acid,
3-hydroxy-5-methylhexanoic acid,
3-hydroxy-5,5-dimethylhexanoic acid,
3-hydroxy-4,4,5-trimethylhexanoic acid,
3-hydroxyheptanoic acid,
3-hydroxy-4-methylheptanoic acid,
3-hydroxy-6-methylheptanoic acid,
3-hydroxy-6,6-dimethylheptanoic acid,
3-hydroxyoctanoic acid,
3-hydroxy-7-methyloctanoic acid,
3-hydroxynonanoic acid,
3-hydroxy-8-methylnonanoic acid,
8-hydroxydecanoic acid,
3-hydroxy-9-methyldecanoic acid,
3-hydroxydecanoic acid,
3-hydroxy-10-methyldecanoic acid,
3-hydroxy-11-methyldodecanoic acid,
3-hydroxy-12-methyltridecanoic acid,
3-hydroxy-4-phenylbutanoic acid,
3-hydroxy-5-phenylpentanoic acid,
3-hydroxy-6-phenylhexanoic acid,
3-hydroxy-7-phenylheptanoic acid,
3-hydroxy-4-(p-methylphenyl)butanoic acid,
3-hydroxy-5-(p-methylphenyl)pentanoic acid,
3-hydroxy-4-(p-methoxylphenyl)butanoic acid,
3-hydroxy-5-(p-methoxylphenyl)pentanoic acid,
3-hydroxy-4-(p-chlorophenyl)butanoic acid,
3-hydroxy-5-(p-chlorophenyl)pentanoic acid, and the like.

The optically active 3-hydroxycarboxylic acid ester (I) can be (3S) form or (3R) form. If it is not a racemic mixture, either (3S) form or (3R) form can be used for the present invention. If the (3R) form of optically active 3-hydroxycarboxylic acid ester (I) is used as a starting material, the optically active 3-halogenocarboxylic acid ester (II) obtained by reaction with thionyl halide is the (3S) form. If the (3S) form of optically active 3-hydroxycarboxylic acid ester (I) is used as a starting material, the optically active 3-halogenocarboxylic acid ester (II) obtained by reaction with thionyl halide is the (3R) form.

The optically active 3-hydroxycarboxylic acid ester (I) used as a starting material of the present invention is a known compound. It can be easily synthesized by a process disclosed in, for example, J. Am. Chem. Soc., 110, 629 (1988), Tetrahedron Lett., 39, 4441(1998), or the like.

Concretely, the optically active 3-hydroxycarboxylic acid ester (I) is produced with a high optical purity by hydrogenation of 3-oxocarboxylic acid ester represented by the formula (V):

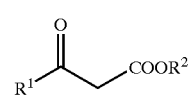

(V)

(wherein $R^1$ and $R^2$ are as defined above) in the presence of an asymmetric hydrogenation catalyst.

A compound represented by the formula $SOX_2$ (wherein X is as defined above) is used as the thionyl halide in the present invention to react with the optically active 3-hydroxycarboxylic acid ester (I). Thionyl chloride, thionyl bromide, and the like can be illustrated. Thionyl chloride is especially preferable because it is cheap and is easy to treat.

It is preferable that the thionyl halaide is used in a range of 1~1.5 mol relative to 1 mol of the optically active 3-hydroxycarboxylic acid ester (I), and more preferably in a range of 1~1.1 mol. If an amount of thionyl halaide is not more than 1 mol relative to 1 mol of the optically active 3-hydroxycarboxylic acid ester (I), an objective optically active 3-halogenocarboxylic acid ester (II) cannot be easily obtained. If an amount of thionyl halaide is greater than 1.5 mol, the reaction rate is increased but an excessive amount of thionyl halide has to be neutralized thus it causes extra cost, time and steps.

In the process of the present invention, reaction of the optically active 3-hydroxycarboxylic acid ester (I) and thionyl halide is performed in the presence of a basic substance. The basic substance acts as a catalyst to replace a hydroxy group at the 3-position of the optically active 3-hydroxycarboxylic acid ester (I) to halogen by reaction with thionyl halide.

An amine is preferable as the basic substance which acts as a catalyst. A primary amine, secondary amine, tertiary amine or aromatic amine can be used. Concretely, an aliphatic amine including aliphatic tertiary amine, for example, triethylamine, diisopropylethylamine, tripropylamine, tributylamine, N-methylpiperidine, N-methylmorpholine, and the like; and an aliphatic secondary amine, for example, diethylamine, dipropylamine, diisopropylamine, dibutylamine, and the like; and an aromatic amine, for example, pyridine, lutidine, picoline, quinoline, and the like, can be illustrated. These amines can be used alone or as a combination of two or more thereof.

An aliphatic amine is preferable from the standpoints that the objective compound, an optically active 3-halogenocarboxylic acid ester (II), can be obtained in a high yield, and of cost. Especially, an aliphatic tertiary amine, for example, triethylamine, diisopropylethylamine, tripropylamine, tributylamine, N-methylpiperidine, N-methylmorpholine, and the like, is more preferable.

The basic substance is used in a catalytic amount. Generally, 0.005~0.5 mol of basic substance relative to 1 mol of the optically active 3-hydroxycarboxylic acid ester (I) is preferable, 0.005~0.2 mol is more preferable, and 0.01~0.05 mol is most preferable.

It is necessary to perform the reaction of the optically active 3-hydroxycarboxylic acid ester (I) with thionyl halide in the presence of the basic substance in an organic solvent in order to obtain the objective compound of optically active 3-halogenocarboxylic acid ester (II) at a high yield. If the reaction of the optically active 3-hydroxycarboxylic acid ester (I) with thionyl halide in the presence of the basic substance is performed without a solvent, the objective compound of optically active 3-halogenocarboxylic acid ester (II) cannot be obtained in a high yield.

As the organic solvent to be used in the present invention, an aliphatic hydrocarbon, for example, pentane, hexane, heptane, and the like; an aromatic hydrocarbon, for example, benzene, toluene, and the like; an ether, for example, diethylether, diisopropylether, tetrahydrofuran, dioxane, dioxolane, dimethoxyethane, and the like; an ester, for example, methyl acetate, ethyl acetate, butyl acetate, methyl propionate, and the like; and a halogenated hydrocarbon, for example, dichloromethane, chloroform, dichloroethane, carbon tetrachloride, and the like; can be illustrated. These organic solvents can be used alone or as a combination of two or more thereof. The aliphatic hydrocarbon including pentane, hexane, heptane, and the like, the aromatic hydrocarbon including benzene, toluene, and the like, and the ether including diethylether, diisopropylether, and the like, are preferable from the standpoints of yield of the objective compound of optically active 3-halogenocarboxylic acid ester (II) and easy operation. The ether including diethylether, diisopropylether, and the like, are most preferable.

The organic solvent is preferably used in a range of 50~500 ml, more preferably 100~200 ml relative to 100 g of the optically active 3-hydroxycarboxylic acid ester (I) when yield of the objective compound of optically active 3-halogenocarboxylic acid ester (II) and industrial efficiency such as shortening of time required to remove the organic solvent after the reaction is completed are considered.

The reaction of the optically active 3-hydroxycarboxylic acid ester (I) with thionyl halide in the organic solvent is preferably performed at −15° C.~110° C., more preferably at 20° C.~110° C. to make the reaction smooth and to obtain the objective compound of optically active 3-halogenocarboxylic acid ester (II) in a high yield.

If necessary, the optically active 3-hydroxycarboxylic acid ester (I) and thionyl halide can be mixed under cooling conditions and heated to a reaction temperature.

A reaction time can be chosen in a range of 2~15 hours, preferably in a range of 4~9 hours.

A recovery or purifying process of the obtained optically active 3-halogenocarboxylic acid ester (II) is not limited. Thus, a conventional process which is used generally can be applied to the present invention. For example, after the reaction is finished, water is added to the reaction system to separate an organic solvent phase and an aqueous phase. The organic solvent phase is recovered and is washed with a base, for example, sodium bicarbonate, and the like, an acid, for example, hydrochloride, citric acid, and the like, a saturated sodium chloride solution, or the like, and then is followed by a process of removal of the organic solvent, such as vacuum distillation, and the like, to obtain the objective compound of the optically active 3-halogenocarboxylic acid ester (II) having a high optical purity with a high yield.

The process described above makes it possible to produce the objective compound of the optically active 3-halogenocarboxylic acid ester (II) having high optical purity with a high yield without a heavy metal salt catalyst, with a simple process, and without racemization.

In the present invention, an optically active 3-halogenocarboxylic acid ester (IT) represented by the formula (II) is produced corresponding to a starting material of optically active 3-hydroxycarboxylic acid ester (I).

Concrete examples of the ester (II) to be produced by the process of the present invention are esters (methyl ester, ethyl ester, n-propyl ester, 2-propyl ester, n-butyl ester, 2-butyl ester, t-butyl ester, 2-methylpropyl ester, and the like) of the following carboxylic acids:

3-chlorobutanoic acid,
2-chloropentanoic acid,
3-chloro-4-methylpentanoic acid,
3-chloro-4-methylhexanoic acid,
3-chlorohexanoic acid,
3-chloro-4-methylhexanoic acid,
3-chloro-5-methylhexanoic acid,
3-chloro-5,5-dimethylhexanoic acid,
3-chloro-4,4,5-trimethylhexanoic acid,
3-chloroheptanoic acid,
3-chloro-4-methylheptanoic acid,
3-chloro-6-methylheptanoic acid,
3-chloro-6,6-dimethylheptanoic acid,
3-chlorooctanoic acid,
3-chloro-7-methyloctanoic acid,
3-chlorononanoic acid,
3-chloro-8-methylnonanoic acid,
3-chlorodecanoic acid,
3-chloro-9-methyldecanoic acid,
3-chloroundecanoic acid,
3-chloro-10-methyldecanoic acid,
3-chloro-11-methyldcdecanoic acid,
3-chloro-12-methyltridecanoic acid,
3-chloro-4-phenylbutanoic acid,
3-chloro-5-phenylpentanoic acid,
3-chloro-6-phenylhexanoic acid,
3-chloro-7-phenylheptanoic acid,
3-chloro-4-(p-methylphenyl)butanoic acid,
3-chloro-5-(p-methylphenyl)pentanoic acid,
3-chloro-4-(p-methoxyphenyl)butanoic acid,
3-chloro-5-(p-methoxyphenyl)pentanoic acid,
3-chloro-4-(p-chlorophenyl)butanoic acid,
3-chloro-5-(p-chlorophenyl)pentanoic acid,
3-bromobutanoic acid,
3-bromopentanoic acid,
3-bromo-4-methylpentanoic acid,
3-bromo-4,4-dimethylpentanoic acid,
3-bromohexanoic acid,
3-bromo-4-methylhexanoic acid, 3-bromo-5-methylhexanoic acid,
3-bromo-5,5-dimethylhexanoic acid,
3-bromo-4,4,5-trimethylhexanoic acid,
3-bromoheptanoic acid,
3-bromo-4-methylheptanoic acid,
3-bromo-6-methylheptanoic acid,
3-bromo-6,6-dimethylheptanoic acid,
3-bromooctanoic acid,
3-bromo-7-methyloctanoic acid,
3-bromononanoic acid,
3-bromo-8-methylnonanoic acid,
3-bromodecanoic acid,
3-bromo-9-methyldecanoic acid,
3-bromoundecanoic acid,
3-bromo-10-methylundecanoic acid,
3-bromo-11-methyldodecanoic acid,
3-bromo-12-methyltridecanoic acid,
3-bromo-4-phenylbutanoic acid,
3-bromo-5-phenylpentanoic acid,
3-bromo-6-phenylhexanoic acid,
3-bromo-7-phenylheptanoic acid,
3-bromo-4-(p-methylphenyl)butanoic acid,
3-bromo-5-(p-methylphenyl)pentanoic acid,
3-bromo-4-(p-methoxyphenyl)butanoic acid,
3-bromo-5-(p-methoxyphenyl)pentanoic acid,
3-bromo-4-(p-chlorophenyl)butanoic acid,
3-bromo-5-(p-chlorophenyl)pentanoic acid, and the like.

The optically active 3-halogenocarboxylic acid ester (II) can be the (3S) form or (3R) form. As explained above, if the (3R) form of optically active 3-hydroxycarboxylic acid ester (I) is used as a starting material, the (3S) form of an optically active 3-halogenocarboxylic acid ester (II) is obtained. If the (3S) form of optically active 3-hydroxycarboxylic acid ester (I) is used as a starting material, the (3R) form of an optically active 3-halogenocarboxylic acid ester (II) is obtained.

Generally, the (3S) form of an optically active 3-halogenocarboxylic acid ester (II) is useful as an intermediate for a medicine, and the (3R) form of an optically active 3-halogenocarboxylic acid ester (II) is useful as an intermediate for a liquid crystal material.

Among the optically active 3-halogenocarboxylic acid esters (II) produced by the method of the present invention, an optically active 3-chlorocarboxylic acid ester represented by the formula (IIa);

(IIa)

(wherein $R^1$, $R^2$ and * are defined above) is especially useful for an intermediate of a medicine and a liquid crystal material as well as being economical.

The optically active 3-halogenocarboxylic acid ester (II) can be the (3S) form or (3R) form as explained above. Unless it is not racemic, either form, i.e., (3S) or (3R) is acceptable. If the (3R) form of optically active 3-halogenocarboxylic acid ester (II) is used, the (3S) form of azide-carboxylic acid ester is obtained by reaction with an azide salt. If the (3S) form of optically active 3-halogenocarboxylic acid ester (II) is used, the (3R) form of an optically active 3-halogenocarboxylic acid ester is obtained by reaction with an azide salt.

The optically active 3-halogenocarboxylic acid ester (II) is a known compound. It is possible to produce the compound by a generally known process, for example, a process taught in J. Org. Chem, 55, 564 (1990), Japanese patent Laid-open Publication No. 63-222148, or the like. However, if the optically active 3-halogenocarboxylic acid ester (II) is produced by the process of the present invention, it is possible to produce the compound in a high yield, with a high optical purity, and with a smooth procedure.

In the present invention, the alkaline metal represented by M in an azide salt represented by the formula $MN_3$ may be lithium, sodium, potassium, rubidium, cesium, and the like. Therefore, as the azide salt reacted with the optically active 3-halogenocarboxylic acid ester (II), lithium azide, sodium azide, potassium azide, rubidium azide, cesium azide, and the like, are illustrated. Sodium azide is preferable from the standpoints that it has a good reactivity with the optically active 3-halogenocarboxylic acid ester (II), and is cheap.

A mol ratio of the azide salt to be used is preferably in a range of 1~20 mol, and more preferably 3~15 mol, relative to 1 mol of the optically active 3-halogenocarboxylic acid ester (II). If the azide salt is used in an amount less than 1 mol relative to 1 mol of the optically active 3-halogenocarboxylic acid ester (II), the objective compound of an optically active 3-azide-carboxylic acid ester (III) is hard to produce smoothly, and if the azide salt is used in an amount of more than 20 mol, it is a problem for operation when the azide salt is not recovered.

In the present invention, the reaction of the optically active 3-halogenocarboxylic acid ester (II) with the azide salt is performed in an aqueous solvent comprising water or a mixture of water and a water soluble organic solvent. This makes it possible to obtain the optically active 3-azide-carboxylic acid ester (III) having a higher optical purity with a higher yield than used to be.

When the reaction of the optically active 3-halogenocarboxylic acid ester (II) with the azide salt is performed in water as the aqueous solvent, it is especially effective to improve optical purity of the optically active 3-azide-carboxylic acid ester (III). When the reaction of the optically active 3-halogenocarboxylic acid ester (II) with the azide salt is performed in the mixture of water and a water soluble organic solvent as the aqueous solvent, the reaction rate is especially good.

If the reaction of the optically active 3-halogenocarboxylic acid ester (II) with the azide salt is performed in a nonaqueous organic solvent or a water soluble organic solvent which does not include water or a mixture of water and a nonaqueous organic solvent instead of the aqueous solvent, yield of the objective compound of optically active 3-azide-carboxylic acid ester (III) or optical purity of the obtained 3-azide-carboxylic acid ester (III) is reduced, and the objects of the present invention cannot be achieved.

When the mixture of water and the water soluble organic solvent is used as the aqueous solvent, a conventional water soluble organic solvent can be used. Concretely, a ketone, for example, acetone, methyl ethyl ketone, and the like; a cyclic ether, for example, tetrahydrofuran, dioxane, dioxolane, and the like; an alcohol, for example, methanol, ethanol, n-propanol, isopropanol, ethylene glycol monoethyl ether, and the like; a polyvalent alcohol, for example, ethylene glycol, propylene glycol, 1,2-propanediol, glycerine, diethylene glycol, and the like; acetonitrile; N-methylpyrrolidone, and the like, are illustrated. These solvents can be used alone or as a combination of two or more thereof. To be used with water, a polyvalent alcohol having not greater than 200 of molecular weight, for example, ethylene glycol, propylene glycol, 1,2-propanediol, glycerine, diethylene glycol, and the like, is preferable.

As the mixture of water and the water soluble organic solvent, it is preferable that water and the water soluble organic solvent are mixed at a ratio of 20:80~80:20 by volume. A ratio of 40:60~60:40 is more preferable and a ratio of 45:55~55:45 is most preferable.

An amount of the aqueous solvent to be used is preferably in a range of 500~5000 ml, more preferably 800~3500 ml, relative to 100 g of the optically active 3-halogenocarboxylic acid ester (II) when yield of the objective compound of optically active 3-azide-carboxylic acid ester (III) and industrial efficiency are considered.

It is preferable to react the optically active 3-halogenocarboxylic acid ester (II) with the azide salt in the mixture of water and the water soluble organic solvent at 20~120° C., more preferably 50~110° C., to make the progress of the reaction smooth, and to obtain the objective compound of optically active 3-azide-carboxylic acid ester (III) with a high yield.

If necessary, the optically active 3-halogenocarboxylic acid ester (II) with the,azide salt can be mixed at cooling condition and be heated to a reaction temperature.

Reaction time may depend on materials but can be chosen in a range of 1~50 hours, preferably in a range of 2~30 hours.

There are no limitations concerning how to recover the objective compound of optically active 3-azide-carboxylic acid ester (III) from a reaction mixture or how to purify it. Conventional treatments can be applied. The following process is an example for recovery and purification. A nonaqueous organic solvent (for example, an aliphatic hydrocarbon, for example, pentane, hexane, heptane, decane, and the like; an aromatic hydrocarbon for example, benzene, toluene, xylene, and the like; an ester, for example, ethyl acetate, and the like; an ether, for example, diethyl ether, diisopropyl ether, and the like; and a halogenated hydrocarbon, for example, dichloromethane, chloroform, dichloroethane, carbon tetrachloride, and the like) may be added to the reaction mixture after the reaction is over to extract the optically active 3-azide-carboxylic acid ester (III) included in the reaction mixture into the nonaqueous organic solvent. Simultaneously, a nonaqueous organic solvent phase is separated from the aqueous phase and is recovered. It is preferable to use a recovered organic solvent as it is for a next reaction, for example, production of an optically active 3-aminocarboxylic acid ester (IV), from the standpoint of operation efficiency.

After the nonaqueous organic solvent phase is separated from the aqueous phase, the aqueous phase contains a unreacted azide salt. It is preferable to use again the aqueous phase containing the unreacted azide salt for a reaction with the optically active 3-halogenocarboxylic acid ester (II) from standpoints of effective use of a material, operating efficiency and reduction of cost. An alkaline metal halide, for example, sodium halide, and the like, which is produced by the reaction of the optically active 3-halogenocarboxylic acid ester (II) with the azide salt, is included in the aqueous phase. When the aqueous phase is reused, it can be used as it is, i.e., containing the alkaline metal halide such as sodium halide, or can be used after the alkaline metal halide is removed. The alkaline metal halide can be removed by filtration.

When the residual azide salt in the aqueous phase is used again for a reaction with the optically active 3-halogenocarboxylic acid ester (II) to produce the optically active 3-azide-carboxylic acid ester (III), an amount of azide salt to be added for the reaction is controlled depending on how much residual azide salt is contained in the aqueous phase. Even the residual azide salt in the aqueous phase is used again as it is to produce the optically active 3-azide-carboxylic acid ester (III), the optically active 3-azide-carboxylic acid ester (III) can be obtained at a high yield and with a high optical purity.

In the present invention, various optically active 3-azide-carboxylic acid esters (III) corresponding to used species of optically active 3-halogenocarboxylic acid esters (II) can be obtained.

As concrete examples of optically active 3-azide-carboxylic acid esters (III), there are esters, for example, methyl ester, ethyl ester, n-propyl ester, 2-propyl ester, n-butylester, 2-butyl ester, t-butyl ester, 2-methylpropyl ester, and the like, of the following carboxylic acids:

3-azide-butanoic acid,
3-azide-pentanoic acid,
3-azide-4-methylpentanoic acid,
3-azide-4-methylhexanoic acid,
3-azide-hexanoic acid,
3-azide-4-methylhexanoic acid,
3-azide-5-methylhexanoic acid,
3-azide-5,5-dimethylhexanoic acid,
3-azide-4,4,5-trimethylhexanoic acid,
3-azide-heptanoic acid,
3-azide-4-methylheptanoic acid,
3-azide-6-methylheptanoic acid,
3-azide-6,6-dimethylheptanoic acid,
3-azide-octanoic acid,
3-azide-7-methyloctanoic acid,
3-azide-nonanoic acid,
3-azide-8-methylnonanoic acid,
3-azide-decanoic acid,
3-azide-9-methyldecanoic acid,
3-azide-undecanoic acid,
3-azide-10-methylundecanoic acid,
3-azide-11-methyldodecanoic acid,
3-azide-12-methyltridecanoic acid,
3-azide-4-phenylbutanoic acid,
3-azide-5-phenylpentanoic acid,
3-azide-6-phenylhexanoic acid,
3-azide-7-phenylheptanoic acid,
3-azide-4-(p-methylphenyl)butanoic acid,
3-azide-5-(p-methylphenyl)pentanoic acid,
3-azide-4-(p-methoxyphenyl)butanoic acid,
3-azide-5-(p-methoxyphenyl)pentanoic acid,
3-azide-4-(p-chlorophenyl)butanoic acid,
3-azide-5-(p-chlorophenyl)pentanoic acid, The optically active 3-azide-carboxylic acid ester (III) produced by the process of the present invention can be the (3S) form or (3R) form. As explained above, if the (3R) form of optically active 3-halogenocarboxylic acid ester (II) is used as a starting material, (3S) form of an optically active 3-azide-carboxylic acid ester (III) is obtained. If the (3S) form of optically active 3-halogenocarboxylic acid ester (II) is used as a starting material, (3R) form of an optically active 3-azide-carboxylic acid ester (III) is obtained.

The optically active 3-azide-carboxylic acid ester (III) obtained by the process explained above is useful as it is or as an intermediate to produce other compounds. An optically active 3-aminocarboxylic acid ester (IV) can be produced with a high yield by hydrogenation of the optically active 3-azide-carboxylic acid ester (III) in the presence of a hydrogenating catalyst.

As the hydrogenating catalyst, any hydrogenating catalyst which has conventionally been used for hydrogenation of the optically active 3-azide-carboxylic acid ester (III) can be used. For example, palladium-carbon, palladium black, platinum oxide, rhodium-carbon, and the like, are illustrated.

An amount of the hydrogenating catalyst to be used is preferably in a range of 1/5000~1/5 g, more preferably 1/2000~1/10 g, relative to 1 g of the optically active 3-azide-carboxylic acid ester (III). If the hydrogenating catalyst is used less than 1/5000 g relative to 1 g of the optically active 3-azide-carboxylic acid ester (III), the optically active 3-aminocarboxylic acid ester (IV) cannot be smoothly obtained. However, if the hydrogenating catalyst is used more than 1/5 g, it costs, and is not good to the environment.

If hydrogenation of the optically active 3-azide-carboxylic acid ester (III) is performed in a nonaqueous organic solvent to make smooth the progress of the hydrogenation, the same nonaqueous organic solvent to be used to extract the optically active 3-azide-carboxylic acid ester can be used. It is preferable to increase operating efficiency. As the nonaqueous organic solvent, an aliphatic hydrocarbon, for example, pentane, hexane, heptane, decane, and the like; an aromatic hydrocarbon, for example, benzene, toluene, xylene, and the like; an ester, for example, ethyl acetate, and the like; an ether, for example, diethyl ether, diisopropyl ether, and the like; and a halogenated hydrocarbon, for example, dichloromethane, chloroform, dichloroethane, carbon tetrachloride, and the like, are illustrated. These solvents can be used alone or in a combination of two or more thereof.

An amount of the nonaqueous organic solvent to be used is preferably 10~10000 ml, more preferably 50~5000 ml, relative to 100 g of the optically active 3-azide-carboxylic acid ester (III).

The hydrogenation to produce the optically active 3-aminocarboxylic acid ester (IV) is preferably performed in the nonaqueous organic solvent phase containing the optically active 3-azide-carboxylic acid ester (III) separated from the reaction mixture containing the optically active 3-azide-carboxylic acid ester (III).

If the hydrogenation to produce the optically active 3-aminocarboxylic acid ester (IV) is performed in the nonaqueous organic solvent phase, the nonaqueous organic solvent which is used to extract the optically active 3-azide-carboxylic acid ester (III) can be used as it is.

The hydrogenation is preferably performed at a temperature of 0~40° C., more preferably 5~35° C., to make the process more smooth and to obtain the optically active 3-aminocarboxylic acid ester (IV) with a high yield and a high optical purity. A reaction time of the hydrogenation is preferably for 30 minutes~30 hours, more preferably 1~25 hours.

There are no limitation as to how to recover the optically active 3-aminocarboxylic acid ester (IV) from a reaction mixture or how to purify it. Conventional treatments can be applied.

As concrete examples of the optically active 3-aminocarboxylic acid ester (IV) produced by the process of the present invention there are esters, for example, methyl ester, ethyl ester, n-propyl ester, 2-propyl ester, n-butylester, 2-butyl ester, t-butyl ester, 2-methylpropyl ester, and the like, of the following carboxylic acids:

3-aminobutanoic acid,
3-aminopentanoic acid,
3-amino-4-methylpentanoic acid,
3-amino-4-methylhexanoic acid,
3-aminohexanoic acid,
3-amino-4-methylhexanoic acid,
3-amino-5-methylhexanoic acid,
3-amino-5,5-dimethylhexanoic acid,
3-amino-4,4,5-trimethylhexanoic acid,
3-aminoheptanoic acid,
3-amino-4-methylheptanoic acid,
3-amino-6-methylheptanoic acid,
3-amino-6,6-dimethylheptanoic acid,
3-aminooctanoic acid,
3-amino-7-methyloctanoic acid,
3-aminononanoic acid,
3-amino-8-methylnonanoic acid,
3-aminodecanoic acid,
3-amino-9-methyldecanoic acid,
3-aminoundecanoic acid,
3-amino-10-methylundecanoic acid,
3-amino-11-methyldodecanoic acid,
3-amino-12-methyltridecanoic acid,
3-amino-4-phenylbutanoic acid,
3-amino-5-phenylpentanoic acid,
3-amino-6-phenylhexanoic acid,
3-amino-7-phenylheptanoic acid,
3-amino-4-(p-methylphenyl)butanoic acid,
3-amino-5-(p-methylphenyl)pentanoic acid,
3-amino-4-(p-methoxyphenyl)butanoic acid,
3-amino-5-(p-methoxyphenyl)pentanoic acid,
3-amino-4-(p-chlorophenyl)butanoic acid,
3-amino-5-(p-chlorophenyl)pentanoic acid, It is preferable to protect an amino group of the optically active 3-aminocarboxylic acid ester (IV) by a protective group, because the amino group of the optically active 3-aminocarboxylic acid ester (IV) is lacking somewhat in stability.

As the protective group, a group described as an amino protecting group in "PROTECTIVE GROUPS IN ORGANIC SYNTHESIS, Second Edition" (John Wiley & sons, Inc.) can be used. Typical protective groups are an acyl type protective group, for example, acetyl, benzoyl, and the like, a urethane type protective group, for example, benzyloxycarbonyl, t-butyloxycarbonyl, and the like.

The optically active 3-aminocarboxylic acid ester (IV) or a compound which an amino group of the optically active 3-aminocarboxylic acid ester (IV) which is protected by a protecting group can be obtained by a simple process and without racemisation with a high yield and a high optical purity.

DESCRIPTION OF PREFERRED EMBODIMENTS

Examples

The present invention is described below in detail in conjunction with examples and is compared with comparative examples. However, it is of course understood that the present invention is not limited to the following examples. The present invention can be modified within the scope and spirit of the appended claims.

In the following examples and comparative examples, a reaction conversion rate, optical rotation ($[\alpha]_D^{20}$), nuclear magnetic resonance ($^1$H-NMR), mass spectrometry, chemical purity and an optical purity of a produced compound were measured as follows:

(1) Reaction Conversion Rate

A reaction conversion rate was calculated from a peak area obtained by gas chromatography (Model No.: 6890A, manufactured by Agilent Technologies).

(2) Optical Rotation ($[\alpha]_D^{20}$)

Model No. DIP-360 manufactured by Nippon Bunkoh Kabushiki Kaisha was used for measurement.

(3) Nuclear Magnetic Resonance ($^1$H-NMR)

Model No. DRX-500 (500 MHZ) manufactured by Bruker Co. Ltd. was used for measurement.

(4) Mass Spectrometry (MS)

Model No. M200A manufactured by Hitachi Seisakusho was used for measurement.

(5) Chemical Purity

Chemical purity (%) of an obtained compound was measured by using gas chromatography (GL) (Model No. TC-WAX manufactured by Science Co., Ltd.) at an initial temperature of 100~150° C., a heating rate of 3° C./min. a temperature of an entrance of the material of 220° C., and a temperature of a detector of 250° C.

(6) Optical Purity (i) Optical purity (%) of each of the compounds produced in Reference Examples 1~5 (an optically active 3-harogenocarboxylic acid ester) and in Examples 1~8 (optically active 3-azide-carboxylic acid ester) was measured by using gas chromatography (Model No. CHIRAL DEXB-TA manufactured by Astec Co., Ltd.) at a constant temperature of 90° C., a temperature of an entrance of a material of 200° C., and a temperature of a detector of 200° C.

(ii) Optical purity (%) of each of the compounds produced in Examples 9~11 was measured by using gas chromatography (Model No. Chrasil-Dex CB manufactured by CHROMPACK Co., Ltd.) at a constant temperature of 115° C., a temperature of an entrance of material of 220° C., and a temperature of a detector of 250° C.

Example 1

Preparation of Methyl(3S)-cholorobutanoate (1) 132.55 g (1.122 mol) of methyl (3R)-hydroxybutanoate (optical purity of 99.5% ee), 265 ml of diisopropyl ether and 7.8 ml (0.056 mol) of triethylamine were mixed. The obtained mixture was cooled to −15° C., and then 40.5 ml (0.561 mol) of thionyl chloride was added dropwise to the chilled mixture. After addition of thionyl chloride was finished, and the mixture was warmed to room temperature, a further 40.5 ml (0.561 mol) of thionyl chloride was added dropwise. After the additional addition of thionyl chloride was finished, the mixture was heated gradually to 75° C. over 7 hours, and then reacted at 75° C. for 10 minutes (reaction conversion rate: 100%).

(2) After the reaction described in (1) was completed, the reaction solution was cooled to not higher than 10° C. ($\leq 10°$ C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 131.9 g of methyl (3S)-chlorobutanoate (yield 86.1%). The obtained methyl (3S)-chlorobutanoate had an optical purity of 98.6% ee, and a boiling point of 70~72° C./4666 Pa (35 mmHg). Its chemical purity was 99.1%.

(3) The optical rotation ($[\alpha]_D^{20}$), $^1$H-NMR and MS of methyl (3S)-chlorobutanoate obtained in (2) were as follows:

$[\alpha]_D^{20}$=+35.0° (c=1.01, CHCl$_3$)

$[\alpha]_D^{20}$=+41.47° (c=1.01, CH$_3$OH)

$^1$H-NMR(CDCl$_3$): δ=1.56(3H, d, J=6.6 Hz), 2.74 (2H, dd, J=6.5, 16.1 Hz), 3.71 (3H, s), 4.3–4.5 (1H, m)

MS: m/z 137 (M$^+$+1)

Examples 2~4

Production of Methyl (3S)-chlorobutanoate (1) 20.00 g (0.169 mol) of methyl (3R)-hydroxybutanoate (optical purity 99.5% ee), 40 ml of each solvent shown in Table 1, and 1.2 ml (8.5 mmol) of triethylamine were mixed. The obtained mixture was cooled to −15° C., and then 6.1 ml (0.085 mol) of thionyl chloride was added dropwise. After addition of thionyl chloride was finished and the mixture was warmed to room temperature, a further 6.1 ml (0.085 mol) of thionyl chloride was added dropwise. Then, the mixture was heated gradually to 75° C. over 6~7 hours, and then reacted at 75° C. for 10 minutes.

(2) After the reaction described in (1) was completed, the reaction solution was cooled to not higher than 10° C. ($\leq 10°$ C.), 80 ml of water was added to separate the reaction mixture into an organic phase and an aqueous phase and to recover the organic phase. The organic phase was washed with 5% sodium bicarbonate solution and saturated sodium chloride solution in sequence. After the solvent was removed, the resultant residue was purified by vacuum distillation to obtain methyl (3S)-chlorobutanoate. The yields (amount and rate), reaction conversion rate and optical purity are shown in Table 1.

TABLE 1

| Example | Solvent | Yield (g) | Yield (%) | Reaction Conversion Rate (%) | Optical Purity (%) |
|---|---|---|---|---|---|
| 2 | Hexane | 16.63 | 71.9 | 98.9 | 99.1 |
| 3 | Dichloromethane | 17.44 | 75.4 | 96.5 | 99.2 |
| 4 | Toluene | 16.54 | 71.5 | 96.1 | 98.9 |

Comparative Example 1

Production of Methyl (3S)-chlorobutanoate 10.00 g (0.085 mol) of methyl (3R)-hydroxybutanoate and 13.09 g (0.10 mol) of thionyl chloride were mixed and were stirred at a room temperature for 20 hours, the mixture was refluxed at 75° C. for an additional 1 hour. The reaction solution was cooled to room temperature, 10 ml of water was added and the solution was extracted with 20 ml of diisopropyl ether. The organic phase was washed with 15 ml of 5% sodium bicarbonate solution and 15 ml of saturated sodium chloride solution in sequence. After the solvent was removed, the resultant residue was checked by gas chromatography. Production of the objective compound of methyl (3S)-chlorobutanoate was not confirmed.

As clear from the results of this comparative example, if an optically active 3-hydroxycarboxylic acid ester (I) and thionyl halide were directly reacted without a basic substance and an organic solvent, an objective compound of an optically active 3-hydroxycarboxylic ester cannot be obtained.

Comparative Example 2

Production of Methyl (3S)-chlorobutanoate 10.00 g (0.085 mol) of methyl (3R)-hydroxybutanoate, 11.10 g (0.093 mol) of thionyl chloride and 0.04 g (0.56 mmol) of pyridine were mixed and were stirred at 60° C. for 3 hours, the mixture was refluxed at 75° C. for 1 hour. The reaction solution was cooled to room temperature, 10 ml of water was added and was extracted with 20 ml of diisopropyl ether. The organic phase was washed with 15 ml of 5% sodium bicarbonate solution and 15 ml of saturated sodium chloride solution in sequence. After the solvent was removed, the resultant residue was purified by vacuum distillation to obtain 6.25 g of methyl (3S)-chlorobutanoate (yield 54%). The obtained methyl (3S)-chlorobutanoate had an optical purity of 97.8% ee, and a boiling point of 70° C./4800 Pa (36 mmHg).

As clear from the results of Comparative Example 2, even if an optically active 3-hydroxycarboxylic acid ester (I) and thionyl halide were reacted in the presence of a basic substance, but if the reaction is not performed in an organic solvent, the yield of objective compound of an optically active 3-hydroxycarboxylic ester (I) is significantly less and the optical purity is also significantly less than that of an optically active 3-hydroxycarboxylic ester (I) produced in the organic solvent.

Comparative Example 3

Production of Methyl (3S)-chlorobutanoate 10.00 g (0.085 mol) of methyl (3R)-hydroxybutanoate, 11.10 g (0.093 mol) of thionyl chloride and 0.05 g (0.50 mmol) of triethylamine were mixed and were stirred at 60° C. for 3 hours, the mixture was refluxed at 75° C. for 1 hour. The reaction solution was cooled to room temperature, 10 ml of water was added and was extracted with 20 ml of diisopropyl ether. The organic phase was washed with 15 ml of 5% sodium bicarbonate solution and 15 ml of saturated sodium chloride solution in sequence. After the solvent was removed, the resultant residue was purified by vacuum distillation to obtain 1.34 g of methyl (3S)-chlorobutanoate (yield 10.0%). The obtained methyl (3S)-chlorobutanoate had an optical purity of 96.0% ee.

As clear from the results of Comparative Example 3, even if an optically active 3-hydroxycarboxylic acid ester (I) and thionyl halide were reacted in the presence of a basic substance, but if the reaction is not performed in an organic solvent, the yield of objective compound of an optically active 3-hydroxycarboxylic ester (I) is significantly less and the optical purity is also significantly less than that of an optically active 3-hydroxycarboxylic ester (I) produced in the organic solvent.

Example 5

Production of Methyl (3S)-chloropentanoate (1) 141.85 g (1.073 mol) of methyl (3R)-hydroxypentanoate (optical purity of 99.4% ee), 284 ml of diisopropyl ether and 7.5 ml (0.054 mol) of triethylamine were mixed. The obtained mixture was cooled to −15° C., and then 38.7 ml (0.537 mol) of thionyl chloride was added dropwise to the chilled mixture. After addition of thionyl chloride was finished, and the mixture was warmed to room temperature, a further 38.7 ml (0.537 mol) of thionyl chloride was added dropwise. After the additional addition of thionyl chloride was finished, the mixture was heated gradually to 75° C. over 6 hours, and then reacted at 75° C. for 30 minutes.

(2) After the reaction described in (1) was completed, the reaction solution was cooled to not higher than 10° C. (≦10° C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 122.97 g of methyl (3S)-chloropentanoate (yield 76.0%). The obtained methyl (3S)-chloropentanoate had an optical purity of 99.2% ee, and a boiling point of 69~70° C./2400 Pa (18 mmHg). Its chemical purity was 98.9%.

(3) The optical rotation ($[\alpha]_D^{20}$), $^1$H-NMR and MS of methyl (3S)-chloropentanoate obtained in (2) were as follows:

$[\alpha]_D^{20}$=+18.3° (c=1.01, CHCl$_3$)
$^1$H-NMR (CDCl$_3$): δ=1.04 (3H, t, J=7.3 Hz), 1.6–1.9 (2H, m), 2.74 (2H, d, J=6.6 Hz), 3.71 (3H, s), 4.1–4.3 (1H, m)
MS: m/z 151 (M$_+$+1)

Example 6

Production of Methyl (3S)-chloroheptanoate (1) 140.85 g (0.879 mol) of methyl (3R)-hydroxyheptanoate (optical purity of 99.6% ee), 280 ml of diisopropyl ether and 6.1 ml (0.044 mol) of triethylamine were mixed. The obtained mixture was cooled to −15° C., and then 31.7 ml (0.440 mol) of thionyl chloride was added dropwise to the chilled mixture. After the addition of thionyl chloride was finished, and the mixture was warmed to room temperature, a further 31.7 ml (0.440 mol) of thionyl chloride was added dropwise. After the additional addition of thionyl chloride was finished, the mixture was heated gradually to 75° C. over 7 hours, and then reacted at 75° C. for 10 minutes.

(2) After the reaction described in (1) was completed, the reaction solution was cooled to not higher than 10° C. (≦10° C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 123.02 g of methyl (3S)-chloroheptanoate (yield 78.3%). The obtained methyl (3S)-chloroheptanoate had an optical purity of 99.2% ee, a chemical purity of 98.6% and a boiling point of 65° C./533.3 Pa (4 mmHg).

(3) The optical rotation ($[\alpha]_D^{20}$), $^1$H-NMR and MS of methyl (3S)-chloroheptanoate obtained in (2) were as follows:

$[\alpha]_D^{20}$=−0.39° (c=1.02, CHCl$_3$)
$^1$H-NMR(CDCl$_3$): δ=0.90(3H, t, J=7.1 Hz), 1.2–1.5(4H, m), 1.65–1.85 (2H, m), 2.74 (2H, d, J=7.0 Hz), 3.71 (3H, s), 4.2–4.4 (1H, m)
MS: m/z 179 (M$^+$+1)

Example 7

Production of Methyl (3S)-chlorooctanoate (1) 145.00 g (0.832 mol) of methyl (3R)-hydroxyoctanoate (optical purity of 99.6% ee), 290 ml of diisopropyl ether and 5.8 ml (0.042 mol) of triethylamine were mixed. The obtained mixture was cooled to −15° C., and then 30.0 ml (0.416 mol) of thionyl chloride was added dropwise to the chilled mixture. After addition of thionyl chloride was finished, and the mixture was warmed to room temperature, a further 30.0 ml (0.416 mol) of thionyl chloride was added dropwise. After the additional addition of thionyl chloride was finished, the mixture was heated gradually to 75° C. over 7 hours, and then reacted at 75° C. for 10 minutes.

(2) After the reaction described in (1) was completed, the reaction solution was cooled to not higher than 10° C. (≦10° C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 126.34 g of methyl (3S)-chlorooctanoate (yield 78.8%). The obtained methyl (3S)-chlorooctanoate had an optical purity of 99.0% ee, a chemical purity of 98.1% and a boiling point of 53~55° C./41.3 Pa (0.31 mmHg).

(3) The optical rotation ($[\alpha]_D^{20}$), $^1$H-NMR and MS of methyl (3S)-chlorooctanoate obtained in (2) were as follows:

$[\alpha]_D^{20}$=−3.70° (c=1.00, CHCl$_3$)

$^1$H-NMR(CDCl$_3$): δ=0.89(3H, t, J=6.6 Hz), 1.2–1.6(6H, m), 1.65–1.8 (2H, m), 2.74 (2H, d, J=6.0 Hz), 3.71 (3H, s), 4.2–4.4 (1H, m)

MS: m/z 193 (M$^+$+1)

Example 8

Production of Methyl (3S)-chlorononanoate (1) 140.00 g (0.744 mol) of methyl (3R)-hydroxynonanoate (optical purity of 99.7% ee), 280 ml of diisopropyl ether and 5.2 ml (0.037 mol) of triethylamine were mixed. The obtained mixture was cooled to −15° C., and then 26.8 ml (0.372 mol) of thionyl chloride was added dropwise to the chilled mixture. After addition of thionyl chloride was finished, and the mixture was warmed to room temperature, a further 26.8 ml (0.372 mol) of thionyl chloride was added dropwise. After the additional addition of thionyl chloride was finished, the mixture was heated gradually to 75° C. over 7 hours, and then reacted at 75° C. for 10 minutes.

(2) After the reaction described in (1) was completed, the reaction solution was cooled to not higher than 10° C. (≦10° C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 117.24 g of methyl (3S)-chlorononanoate (yield 76.3%). The obtained methyl (3S)-chlorononanoate had an optical purity of 99.3% ee and a boiling point of 65° C./29.3 Pa (0.22 mmHg).

(3) The optical rotation ($[\alpha]_D^{20}$), $^1$H-NMR and MS of methyl (3S)-chlorononanoate obtained in (2) were as follows:

$[\alpha]_D^{20}$=−4.01° (c=1.02, CHCl$_3$)

$^1$H-NMR(CDCl$_3$): δ=0.88(3H, t, J=6.6 Hz), 1.2–1.6(8H, m), 1.65–1.8 (2H, m), 2.75 (2H, d, J=7.0 Hz), 3.72 (3H, s), 4.2–4.4 (1H, m)

MS: m/z 207 (M$^+$+1)

Example 9

Production of Methyl (3S)-chloro-5-methylhexanoate (1) 140.00 g (0.874 mol) of methyl (3R)-hydroxy-5-methylhexanoate (optical purity of 99.6% ee), 280 ml of diisopropyl ether and 6.1 ml (0.044 mol) of triethylamine were mixed. The obtained mixture was cooled to −15° C., and then 31.5 ml (0.437 mol) of thionyl chloride was added dropwise to the chilled mixture. After addition of thionyl chloride was finished, and the mixture was warmed to room temperature, a further 31.5 ml (0.437 mol) of thionyl chloride was added dropwise. After the additional addition of thionyl chloride was finished, the mixture was heated gradually to 75° C. over 7 hours, and then reacted at 75° C. for 10 minutes.

(2) After the reaction described in (1) was completed, the reaction solution was cooled to not higher than 10° C. (≦10° C.), 80 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 108.86 g of methyl (3S)-chloro-5-methylhexanoate (yield 69.8%) The obtained methyl (3S)-chloro-5-methylhexanoate had an optical purity of 99.0% ee, a chemical purity of 98.4% and a boiling point of 44° C./73.3 Pa (0.55 mmHg).

(3) The optical rotation ($[\alpha]_D^{20}$), $^1$H-NMR and MS of methyl (3S)-chloro-5-methylhexanoate obtained in (2) were as follows:

$[\alpha]_D^{20}$=−18.8° (c=1.02, CHCl$_3$)

$^1$H-NMR(CDCl$_3$): δ=0.92(3H, d, J=6.6 Hz), 0.93 (3H, d, J=6.6 Hz), 1.4–1.8 (2H, m), 1.8–2.0 (1H, m), 2.73 (2H, d, J=7.4 Hz), 3.72 (3H, s), 4.25–4.41 (1H, m)

MS: m/z 179 (M$^+$+1)

Example 10

Production of Methyl (3S)-chlorobutanoate (1) 10.00 g (0.085 mol) of methyl (3R)-hydroxybutanoate (optical purity of 99.5% ee), 20 ml of diisopropyl ether, 11.1 ml (0.093 mol) of thionyl chloride and 0.04 g (0.56 mmol) of pyridine were mixed and were stirred at 60° C. for 3 hours, the mixture was refluxed at 75° C. for 1 hour.

(2) After the reaction described in (1) was completed, the reaction solution was cooled to room temperature, 10 ml of water was added to separate the reaction mixture into an organic phase and an aqueous phase and to recover the organic phase. The organic phase was washed with 160 ml of 5% sodium bicarbonate solution and 160 ml of saturated sodium chloride solution in sequence. After the solvent was removed, the resultant residue was purified by vacuum distillation to obtain 8.91 g of methyl (3S)-chlorobutanoate (yield 72.9%). The obtained methyl (3S)-chlorobutanoate had an optical purity of 99.5% ee of and a boiling point of 70° C./4800 Pa (36 mmHg).

Example 11

Production of Methyl (3R)-azide-butanoate 10.00 g (0.0738 mol) of methyl (3S)-chlorobutanoate (optical purity obtained 98.6% ee) in Example 1, 200 ml of distilled water and 48.00 g (0.738 mol) of sodium azide were mixed, and were stirred to react at 94–96° C. for 3 hours. After a reaction conversion rate was checked by gas chromatography and was confirmed to be more than 99%, the reaction solution was cooled to room temperature. 30 ml of toluene was added to the reaction solution and shaken to extract the reaction resultant and was separated into an aqueous phase and a toluene phase to recover the toluene phase containing methyl (3R)-azide-butanoate. When the toluene phase was examined by gas chromatography, the yield of methyl (3R)-azide-butanoate was 65.3%, and the optical purity was 98.0% ee.

Comparative Example 4

Production of Methyl (3R)-azide-butanoate 0.50 g (3.69 mol) of methyl (3S)-chlorobutanoate obtained in Example 1, 0.262 g (4.03 mmol) of sodium azide and 1.0 ml of N,N-dimethylformamide were mixed, and were stirred to react at 81° C. for 3 hours. Then the reaction solution was checked by gas chromatography to obtain a reaction conversion rate. The reaction conversion rate was 100%. The selection rate of the obtained methyl (3R)-azide-butanoate was 87.7%, and the yield was 75%. The obtained methyl (3R)-azide-butanoate had an optical purity of 4.7% ee.

The results of Comparative Example 4 shows that when the reaction of methyl (3S)-chlorobutanoate with sodium azide is not performed in water or a mixture of water and a water soluble organic solvent, and is performed in N,N-dimethylformamide, methyl (3R)-azide-butanoate has a lower optical purity.

Comparative Example 5

Production of Methyl (3R)-azide-butanoate 0.50 g (3.69 mol) of methyl (3S)-chlorobutanoate obtained in Example 1, 0.24 g (3.69 mmol) of sodium azide and 1.0 ml of dimethyl sulfoxide were mixed, and were stirred to react at 81° C. for 3 hours. Then the reaction solution was checked by gas chromatography to obtain a reaction conversion rate. The reaction conversion rate was 100%. The selection rate of the obtained methyl (3R)-azide-butanoate was 40.6%, and the yield was 36%. The obtained methyl (3R)-azide-butanoate had an optical purity of 5.1% ee.

The results of Comparative Example 5 shows that when the reaction of methyl (3S)-chlorobutanoate with sodium azide is not performed in water or a mixture of water and a water soluble organic solvent, and is performed in dimethyl sulfoxide, methyl (3R)-azide-butanoate has a low optical purity as well as a low yield.

Comparative Example 6

Production of Methyl (3R)-azide-butanoate 0.50 g (3.69 mol) of methyl (3S)-chlorobutanoate obtained in Example 1, 0.262 g (4.03 mmol) of sodium azide and 0.50 g of polyethylene glycol (#2000), 0.5 ml of water and 1 ml of toluene were mixed, and were stirred to react at 81° C. for 3 hours and 40 minutes. Then the reaction solution was checked by gas chromatography to obtain a reaction conversion rate. The reaction conversion rate was 9.07%. The selection rate of the obtained methyl (3R)-azide-butanoate was 41.8%, and the yield was 6.5%. The obtained methyl (3R)-azide-butanoate had an optical purity of 96% ee.

The results of Comparative Example 6 showed that when the reaction of methyl (3S)-chlorobutanoate with sodium azide was not performed in water or a mixture of water and a water soluble organic solvent, and was performed in a water/toluene mixture containing polyethylene glycol, the yield of methyl (3R)-azide-butanoate was low.

Example 12

Production of Methyl (3R)-azide-butanoate (1) 20.00 g (0.1477 mol) of methyl (3S)-chlorobutanoate (optical purity 98.6% ee) obtained in the same manner as Example 1, 200 ml of distilled water and 96.00 g (1.477 mol) of sodium azide were mixed, and were stirred to react at 94~96° C. for 4 hours and 30 minutes. After the reaction conversion rate was checked by gas chromatography and confirmed completion of the reaction, the reaction solution was cooled to room temperature. 60 ml of toluene was added to the reaction solution and shaken to extract the reaction resultant and was separated into an aqueous phase and a toluene phase to recover 66.4 g of the toluene solution containing methyl (3R)-azide-butanoate. The separated water phase containing unreacted sodium azide was used in Example 13.

(2) The toluene solution recovered in (1) was examined by gas chromatography, and the yield of methyl (3R)-azide-butanoate was 61.9%, and the optical purity was 97.8% ee.

Example 13

Production of Methyl (3R)-azide-butanoate: Reuse of Water Phase Containing Unreacted Sodium Azide (1) 20.00 g (0.1477 mol) of methyl (3S)-chlorobutanoate (optical purity 98.6% ee) obtained in the same manner as Example 1, the entire water phase separated in (1) of Example 12 (245 ml) and 9.60 g (0.1477 mol) of sodium azide were mixed, and were stirred to react at 94~96° C. for 5 hours. Then the reaction conversion rate was checked by gas chromatography. The reaction conversion rate was 98.8%. After the reaction was finished, the reaction solution was cooled to room temperature. 60 ml of toluene was added to the reaction solution and shaken to extract the reaction resultant and was separated into an aqueous phase and a toluene phase to recover 67.36 g of the toluene solution containing methyl (3R)-azide-butanoate. 250 ml of the separated water phase containing unreacted sodium azide was used in Example 14.

(2) The toluene solution recovered in (1) was examined by gas chromatography, and the yield of methyl (3R)-azide-butanoate was 64.6%, and the optical purity was 97.8% ee.

Example 14

Production of Methyl (3R)-azide-butanoate: Reuse of Water Phase Containing Unreacted Sodium Azide (1) 20.00 g (0.1477 mol) of methyl (3S)-chlorobutanoate (optical purity 98.6% ee) obtained in the same manner as Example 1, the entire water phase separated in (1) of Example 13 (250 ml) and 9.60 g (0.1477 mol) of sodium azide were mixed, and were stirred to react at 94~96° C. for 6 hours. Then the reaction conversion rate was checked by gas chromatography. The reaction conversion rate was 98.0%. After the reaction was finished, the reaction solution was cooled to room temperature. 60 ml of toluene was added to the reaction solution and shaken to extract the reaction resultant and was separated into an aqueous phase and a toluene phase to recover 67.10 g of the toluene solution containing methyl (3R)-azide-butanoate. 255 ml of the separated water phase containing unreacted sodium azide was used in (2) below. The toluene solution recovered in (1) was examined by gas chromatography, and the yield of methyl (3R)-azide-butanoate was 62.5%, and the optical purity was 96.2% ee.

(2) 20.00 g (0.1477 mol) of methyl (3S)-chlorobutanoate (optical purity 98.6% ee) obtained in the same manner as Example 1, the entire water phase separated in (1) (255 ml)

and 9.60 g (0.1477 mol) of sodium azide were mixed, and were stirred to react at 94~96° C. for 6 hours and 40 minutes. Then the reaction conversion rate was checked by gas chromatography. The reaction conversion rate was 98.1%. After the reaction was finished, the reaction solution was cooled to room temperature. 60 ml of toluene was added to the reaction solution and shaken to extract the reaction resultant and was separated into an aqueous phase and a toluene phase to recover 66.00 g of the toluene solution containing methyl (3R)-azide-butanoate. 260 ml of the separated water phase containing unreacted sodium azide was used in (3) below. The recovered toluene solution was examined by gas chromatography, and the yield of methyl (3R)-azide-butanoate was 57.7%, and the optical purity was 95.2% ee.

(3) 20.00 g (0.1477 mol) of methyl (3S)-chlorobutanoate (optical purity 98.6% ee) obtained in the same manner as Example 1, the entire water phase separated in (2) (260 ml) and 9.60 g (0.1477 mol) of sodium azide were mixed, and were stirred to react at 94~96° C. for 7 hours. Then a reaction conversion rate was checked by gas chromatography. The reaction conversion rate was 98.0%. After the reaction was finished, the reaction solution was cooled to room temperature. 60 ml of toluene was added to the reaction solution and shaken to extract the reaction resultant and was separated into an aqueous phase and a toluene phase to recover 64.80 g of the toluene solution containing methyl (3R)-azide-butanoate. The recovered toluene solution was examined by gas chromatography, and the yield of methyl (3R)-azide-butanoate was 52.8%, and the optical purity was 94.1% ee.

Example 15

Production of Methyl (3R)-azide-pentanoate 1.00 g (6.64 mmol) of methyl (3S)-chloropentanoate (optical purity 99.2% ee) obtained in the same manner as Example 5, 20 ml of distilled water and 4.32 g (66.4 mmol) of sodium azide were mixed, and were stirred to react at 94~96° C. for 9 hours. The reaction conversion rate obtained by gas chromatography was 100%. After the reaction was finished, the reaction solution was cooled to room temperature and 5 ml of heptane was added and was stirred to separate into an aqueous phase and a heptane phase. 5.10 g of the heptane solution containing methyl (3R)-azide-pentanoate was separated and was recovered. The recovered heptane solution was examined by gas chromatography. The yield of methyl (3R)-azide-heptanoate was 68.3%, and the optical purity was 99.2% ee.

Example 16

Production of Methyl (3R)-azide-5-methylhexanoate 1.00 g (5.60 mmol) of methyl (3S)-chloro-5-methylhexanoate (optical purity 99.0% ee) obtained in the same manner as Example 9, 20 ml of distilled water and 3.64 g (56.0 mmol) of sodium azide were mixed, and were stirred to react at 94~96° C. for 23 hours. The reaction conversion rate obtained by gas chromatography was 69.4%. After the reaction was finished, the reaction solution was cooled to room temperature and 5 ml of heptane was added and was stirred to separate into an aqueous phase and a heptane phase. 5.10 g of the heptane solution containing methyl (3R)-azide-5-methylhexanoate was separated and was recovered. The recovered heptane solution was examined by gas chromatography. The methyl (3R)-azide-5-methylhexanoate had an optical purity of 99.0% ee.

Example 17

Production of Methyl (3R)-azide-heptanoate 1.00 g (5.60 mmol) of methyl (3S)-chloroheptanoate (optical purity 99.2% ee) obtained in the same manner as Example 6, 3.64 g (56.0 mmol) of sodium azide, 10 ml of diethylene glycol and 10 ml of distilled water were mixed, and were stirred to react at 94~96° C. for 9 hours. Then the reaction conversion rate obtained by gas chromatography was 97.6%. After the reaction was finished, the reaction solution was cooled to room temperature and 5 ml of toluene was added and was stirred to separate into an aqueous phase and a toluene phase. 5.20 g of the toluene solution containing methyl (3R)-azide-heptanoate was separated and was recovered. The recovered toluene solution was examined by gas chromatography. The methyl (3R)-azide-heptanoate had an optical purity of 95.4% ee.

Example 18

Production of Methyl (3R)-azide-octanoate 1.00 g (5.19 mmol) of methyl (3S)-chlorooctanoate (optical purity 99.0% ee) obtained in the same manner as Example 7, 3.37 g (51.9 mmol) of sodium azide, 10 ml of diethylene glycol and 10 ml of distilled water were mixed, and were stirred to react at 94~96° C. for 23 hours. Then the reaction conversion rate obtained by gas chromatography was 100.0%. After the reaction was finished, the reaction solution was cooled to room temperature and 5 ml of toluene was added and was stirred to separate into a aqueous phase and a toluene phase. 5.30 g of the toluene solution containing methyl (3R)-azide-octanoate was separated and was recovered. The recovered toluene solution was examined by gas chromatography. The methyl (3R)-azide-octanoate had an optical purity of 91.9% ee.

Example 19

Production of Methyl (3R)-aminobutanoate and Protection of Amino Group (1) 0.21 g of 5% Pd—C (a palladium-carbon catalyst) was added to 67.10 g of of the toluene solution of methyl (3R)-azide-butanoate (optical purity 97.8% ee) obtained in the same manner as Example 13, hydrogen gas was provided into the solution with a pressure of 2 MPa in an SUS autoclave having 120 ml capacity at room temperature to hydrogenate under pressure for 24 hours. Then it was confirmed by gas chromatography that methyl (3R)-azide-butanoate was present in a trace amount.

(2) After the reaction was finished, the reaction solution was filtered. 18.09 g (0.177 mol) of acetic anhydride was added to the filtrate to acetylate at room temperature for 4 hours. After the reaction was completed, toluene was recovered under vacuum to obtain 13.80 g of methyl (3R)-acetylaminobutanoate (methyl-(3R)-acetoamidobutanoate) in which the amino group was protected by an acetyl group (yield 58.6%) by vacuum distillation. The obtained methyl (3R)-acetylaminobutanoate had an optical purity of 98.1% ee, a chemical purity of 99.6% and a boiling point of 79° C./21.4 Pa (0.16 mmHg).

(3) The optical rotation ($[\alpha]_D^{20}$), 1H-NMR and MS of methyl (3R)-acetylaminobutanoate obtained in (2) were as follows:

[α]$_D^{20}$=+25.43° (c=1.03, CH$_3$OH)

$^1$H-NMR(CDCl$_3$): δ=1.23 (3H, d, J=6.8), 1.96 (3H, s), 2.53 (2H, dd, J=2.1, 5.3), 3.7 (3H, s), 4.53 (1H, m), 6.15 (1H, d)

MS: m/z 159 (M$^+$+1)

Example 20

Production of Methyl (3R)-aminopentanoate and Protection of Amino Group (1) 10.00 g (0.0660 mol) of methyl (3S)-chloropentanoate (optical purity 99.2% ee) obtained in the same manner as Example 5, 200 ml of water and 43.17 g (0.6640 mol) of sodium azide were mixed, and were stirred to react at 97° C. for 9 hours. Then the reaction solution was cooled to room temperature. The objective compound was extracted twice with 10 ml of heptane. Each time the heptane phase was separated.

(2) Both separated heptane phases were combined, and were transferred to an autoclave having 100 ml capacity. 104.4 mg of 5% Pd—C was added. Hydrogen gas having a pressure of 1.5 Mpa was provided to the autoclave for hydrogenation at room temperature under pressure for 15 hours. The reaction solution was filtered. 7.12 g (0.0697 mol) of acetic anhydride was added to the filtration, and the solution was stirred to react for 2.5 hours. Then the solvent, heptane, was removed by distillation, and 6.51 g of methyl (3R)-acetylaminopentanoate (yield 56.6%) was obtained after vacuum distillation. The obtained methyl (3R)-acetylaminopentanoate had an optical purity of 98.5% ee, a chemical purity of 100%, a boiling point of 85° C./14.7 Pa (0.11 mmHg) and a melting point of 49.0~50.3° C.

(3) The optical rotation ([δ]$_D^{20}$), $^1$H-NMR and MS of methyl (3R)-acetylaminopentanoate obtained in (2) were as follows:

[α]$_D^{20}$=+58.5° (c=1.00, CHCl$_3$)

$^1$H-NMR(200 MHz, CDCl$_3$) δ=0.91(3H, t, J=7.4 Hz), 1.5–1.7 (2H, m), 1.97 (3H, s), 2.54 (2H, dd, J=1.7, 5.1), 3.68 (3H, s), 4.1–4.3 (1H, m), 6.00 (1H, brs)

MS: m/z 174 (M$^+$+1)

Example 21

Production of Methyl (3R)-aminoheptanoate and Protection of Amino Group (1) 10.00 g (0.0560 mol) of methyl (3S)-chloroheptanoate (optical purity 99.2% ee) obtained in the same manner as Example 9, 100 ml of water, 100 ml of diethylene glycol and 43.17 g (0.6640 mol) of sodium azide were mixed, and were stirred to react at 97° C. for 23 hours. Then the reaction solution was cooled to room temperature. The objective compound was extracted twice with 10 ml of heptane. Each time the heptane phase was separated.

(2) Both separated heptane phases were combined, and were transferred to an autoclave having 100 ml capacity. 103.7 mg of 5% Pd—C was added. Hydrogen gas having pressure of 1.5 Mpa was provided to the autoclave for hydrogenation at room temperature under pressure for 15 hours. The reaction solution was filtered. 6.00 g (0.0588 mol) of acetic anhydride was added to the filtrate, and the solution was stirred to react for 2.5 hours. Then the solvent, heptane, was removed by distillation, and 3.34 g of methyl (3R)-acetylaminoheptanoate (yield 29.6%) was obtained after vacuum distillation. The obtained methyl (3R)-acetylaminoheptanoate had an optical purity of 95.0% ee, a chemical purity of 97.0%, a boiling point of 100° C./12.0 Pa (0.09 mmHg) and a melting point of 49.2° C.

(3) The optical rotation ([α]$_D^{20}$), $^1$H-NMR and MS of methyl (3R)-acetylaminoheptanoate obtained in (2) were as follows:

[α]$_D^{20}$=+30.7° (c=1.00, CHCl$_3$)

$^1$H-NMR(200 MHz, CDCl$_3$) δ=0.87(3H, t, J=6.8 Hz), 1.2–1.4 (4H, m) 1.4–1.6 (2H, m), 1.96 (3H, s), 2.52 (2H, dd, J=3.1, 5.1), 3.67 (3H, s), 4.1–4.3 (1H, m), 6.03 (1H, d, J=8.2)

MS: m/z 202 (M$^+$+1)

ADVANTAGES OF THE INVENTION

According to the process of the present invention, a desired optically active 3-halogenocarboxylic acid ester (II) can be produced without using a heavy metal salt catalyst and is free of racemization. Besides such advantages, the ester can be obtained with a high yield and high optical purity.

An optically active 3-halogenocarboxylic acid ester (II) is very useful as an intermediate for medicines, liquid crystal materials, and the like.

According to the process of the present invention, a desired optically active 3-azide-carboxylic acid ester (III) and 3-aminocarboxylic acid ester (IV) also can be obtained with a high yield and high optical purity.

Furthermore, according to the process of the present invention, it is possible to recover and separate unreacted azide salt that is used for azidation from a reaction mixture in a condition of being dissolved in an aqueous solution comprising water or a mixture of water and a hydrophilic organic solvent. The recovered unreacted azide salt can be used repeatedly as contained in the aqueous solution without separation. Therefore, its operating efficiency is very good, and it is excellent from the standpoints of effective recycle of reaction agent and reduction of cost.

The optically active 3-azide-carboxylic acid ester (III) and 3-aminocarboxylic acid ester (IV) produced by the process of the present invention are very useful as an intermediate for medicines, liquid crystal materials, and the like.

What is claimed is:

1. A process for producing an optically active 3-azide-carboxylic acid ester comprising reacting an optically active 3-hydroxycarboxylic acid ester represented by the following formula (I);

(I)

(wherein R$^1$ is alkyl, substituted alkyl, aralkyl or substituted aralkyl; R$^2$ is lower alkyl; and * is an asymmetric carbon) with a thionyl halide in the presence of a basic substance in an organic solvent to produce an optically active 3-halogenocarboxylic acid ester represented by the following formula (II);

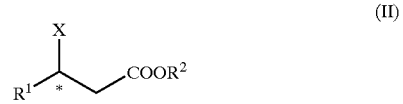

(II)

(wherein X is halogen, and R$^1$, R$^2$ and * are as defined above); and the optically active 3-halogenocarboxylic acid ester represented by the formula (II) is reacted with an azide salt represented by the formula: $MN_3$ (wherein M is alkaline metal) in an aqueous solvent to produce an optically active 3-azide-carboxylic acid ester represented by the following formula (III);

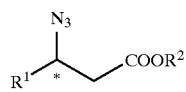

(III)

(wherein $R^1$, $R^2$ and * are as defined above).

2. A process for producing an optically active 3-aminocarboxylic acid ester comprising reacting an optically active 3-hydroxycarboxylic acid ester represented by the following formula (I);

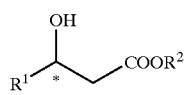

(I)

(wherein $R^1$ is alkyl, substituted alkyl, aralkyl or substituted aralkyl; $R^2$ is lower alkyl; and * is an asymmetric carbon) with a thionyl halide in the presence of a basic substance in an organic solvent to produce an optically active 3-halogenocarboxylic acid ester represented by the following formula (II);

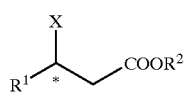

(II)

(wherein X is halogen, and $R^1$, $R^2$ and * are as defined above); reacting the optically active 3-halogenocarboxylic acid ester represented by the formula (II) with an azide salt represented by the formula: $MN_3$ (wherein M is alkaline metal) in an aqueous solvent to produce an optically active 3-azide-carboxylic acid ester represented by the following formula (III);

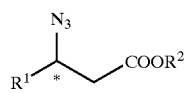

(III)

(wherein $R^1$, $R^2$ and * are as defined above); and then hydrogenating the 3-azide-carboxylic acid ester in the presence of a hydrogenating catalyst to produce an optically active 3-aminocarboxylic acid ester represented by the formula (IV);

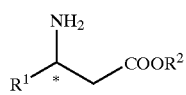

(IV)

(wherein $R^1$, $R^2$ and * are as defined above).

3. A process for producing an optically active 3-halogenocarboxylic acid ester comprising reacting an optically active 3-hydroxycarboxylic acid ester represented by the following formula (I);

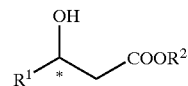

(I)

(wherein $R^1$ is alkyl, substituted alkyl, aralkyl or substituted aralkyl; $R^2$ is lower alkyl; and * is an asymmetric carbon) with a thionyl halide in the presence of a basic substance in an organic solvent to produce an optically active 3-halogenocarboxylic acid ester represented by the following formula (II);

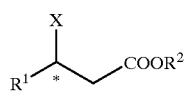

(II)

(wherein X is halogen, $R^1$, $R^2$ and * are as defined above).

4. The process for producing an optically active 3-chlorocarboxylic acid ester according to claim 3, wherein the thionyl halide is thionyl chloride to produce an optically active 3-chlorocarboxylic acid ester represented by the formula (IIa);

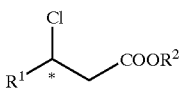

(IIa)

(wherein $R^1$ is alkyl, substituted alkyl, aralkyl or substituted aralkyl; $R^2$ is lower alkyl; and * is an asymmetric carbon).

5. The process for producing an optically active 3-chlorocarboxylic acid ester according to claim 3, wherein the basic substance is an amine.

6. A process for producing an optically active 3-azide-carboxylic acid ester comprising reacting an optically active 3-halogenocarboxylic acid ester represented by the following formula (II);

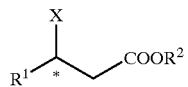

(II)

(wherein X is halogen; $R^1$ is alkyl, substituted alkyl, aralkyl or substituted aralkyl; $R^2$ is lower alkyl; and * is an asymmetric carbon) with an azide salt represented by the formula: $MN_3$ (wherein M is alkaline metal) in water or a mixture of water and a polyvalent alcohol to produce an optically active 3-azide-carboxylic acid ester represented by the following formula (III);

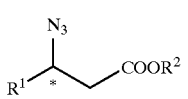

(III)

(wherein $R^1$, $R^2$ and * are as defined above).

7. The process for producing an optically active 3-azide-carboxylic acid ester according to claim 6, wherein the reaction of the 3-halogenocarboxylic acid ester with the azide salt is carried out in the mixture of water and a polyvalent alcohol.

8. The process for producing an optically active 3-azide-carboxylic acid ester according to claim 6, wherein the azide salt used for producing the optically active 3-azide-carboxylic acid ester represented by the formula (III) is recovered from a reaction mixture containing the produced optically active 3-azide-carboxylic acid ester.

9. The process for producing an optically active 3-azide-carboxylic acid ester according to claim 6, wherein the azide salt used for production of the optically active 3-azide-carboxylic acid ester represented by the formula (III) is recovered from a reaction mixture containing the produced optically active 3-azide-carboxylic acid ester, and the recovered azide salt is used again for reaction with an optically active 3-halogenocarboxylic acid ester represented by the formula (II).

10. The process for producing an optically active 3-azide-carboxylic acid ester according to claim 6, wherein the azide salt is recovered as an aqueous phase with the water or the mixture or water and a polyvalent alcohol.

11. A process for producing an optically active 3-aminocarboxylic acid ester comprising reacting an optically active 3-halogenocarboxylic acid ester represented by the following formula (II);

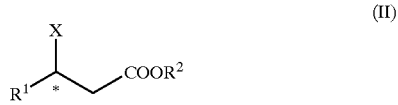

(II)

(wherein X is halogen; $R^1$ is alkyl, substituted alkyl, aralkyl or substituted aralkyl; $R^2$ is lower alkyl; and * is an asymmetric carbon) with an azide salt represented by the formula: $MN_3$ (wherein M is alkaline metal) in water or a mixture of water and polyvalent alcohol to produce an optically active 3-azide-carboxylic acid ester represented by the following formula (III);

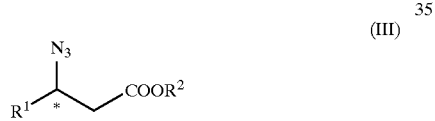

(III)

(wherein $R^1$, $R^2$ and * are as defined above); and then hydrogenating the optically active 3-azide-carboxylic acid ester in the presence of a hydrogenation catalyst to produce an optically active 3-aminocarboxylic acid ester represented by the formula (IV);

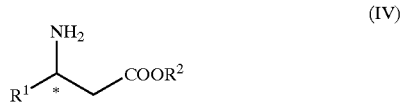

(IV)

(wherein $R^1$, $R^2$ and * are as defined above).

12. The process for producing an optically active 3-aminocarboxylic acid ester according to claim 11, wherein the reaction of the 3-halogenocarboxylic acid ester with the azide salt is carried out in the mixture of water and a polyvalent alcohol.

13. The process for producing an optically active 3-aminocarboxylic acid ester according to claim 11, wherein the azide salt used for producing the optically active 3-azide-carboxylic acid ester represented by the formula (III) is recovered from a reaction mixture containing the produced optically active 3-azide-carboxylic acid ester.

14. The process for producing an optically active 3-aminocarboxylic acid ester according to claim 11, wherein the azide salt used for producing of the optically active 3-azide-carboxylic acid ester represented by the formula (III) is recovered from a reaction mixture containing the produced optically active 3-azide-carboxylic acid ester, and the recovered azide salt is used again for reaction with an optically active 3-halogenocarboxylic acid ester represented by the formula (II).

15. The process for producing an optically active 3-aminocarboxylic acid ester according to claim 11, wherein the azide salt is recovered as an aqueous phase with the water or the mixture of water and a polyvalent alcohol.

16. The process for producing an optically active 3-azidecarboxylic acid ester according to claim 6, wherein the optically active 3-halogenocarboxylic acid ester represented by the formula (II) is an optically active 3-chlorocarboxylic acid ester represented by the formula (IIa);

(IIa)

(wherein $R^1$ is alkyl, substituted alkyl, aralkyl or substituted aralkyl; $R^2$ is lower alkyl; and * is an asymmetric carbon).

17. The process for producing an optically active 3-aminocarboxylic acid ester according to claim 11, wherein the optically active 3-halogenocarboxylic acid ester represented by the formula (II) is an optically active 3-chlorocarboxylic acid ester represented by the formula (IIa);

(IIa)

(wherein $R^1$ is alkyl, substituted alkyl, aralkyl or substituted aralkyl; $R^2$ is lower alkyl; and * is an asymmetric carbon).

* * * * *